US012662452B2

(12) United States Patent
Muthusamy et al.

(10) Patent No.: US 12,662,452 B2
(45) Date of Patent: Jun. 23, 2026

(54) SOLID STATE FORMS OF LUCERASTAT AND PROCESS FOR PREPARATION THEREOF

(71) Applicant: ASSIA CHEMICAL INDUSTRIES LTD., Tel Aviv (IL)

(72) Inventors: Anantha Rajmohan Muthusamy, Sivakasi (IN); Sundara Lakshmi Kanniah, Vellore (IN); Yogesh Dhananjay Wagh, Thane (IN)

(73) Assignee: ASSIA CHEMICAL INDUSTRIES LTD., Tel Aviv (IL)

( * ) Notice: Subject to any disclaimer, the term of this patent is extended or adjusted under 35 U.S.C. 154(b) by 1001 days.

(21) Appl. No.: 17/762,443

(22) PCT Filed: Sep. 23, 2020

(86) PCT No.: PCT/US2020/052110

§ 371 (c)(1),
(2) Date: Mar. 22, 2022

(87) PCT Pub. No.: WO2021/061701

PCT Pub. Date: Apr. 1, 2021

(65) Prior Publication Data

US 2022/0411371 A1 Dec. 29, 2022

(30) Foreign Application Priority Data

Sep. 25, 2019 (IN) ............................ 201911038702
Oct. 25, 2019 (IN) ............................ 201911043541

(51) Int. Cl.
*C07D 211/46* (2006.01)

(52) U.S. Cl.
CPC ........ *C07D 211/46* (2013.01); *C07B 2200/13* (2013.01)

(58) Field of Classification Search
None
See application file for complete search history.

(56) References Cited

U.S. PATENT DOCUMENTS 6,291,657 B1 9/2001 Platt et al.

FOREIGN PATENT DOCUMENTS

WO WO/1995/22975 * 2/1995 ........... A61K 31/445
WO 2018220131 A1 12/2018
WO WO 2018/220131 * 12/2018 ........... C07D 211/46

OTHER PUBLICATIONS

International Search Report and Written Opinion of the International Searching Authority issued in corresponding application PCT/US2020/052110 mailed Jan. 19, 2021 (12 pages).

* cited by examiner

*Primary Examiner* — Craig D Ricci
(74) *Attorney, Agent, or Firm* — Carter, DeLuca & Farrell, LLP

(57) ABSTRACT

The present disclosure encompasses solid state forms of Lucerastat, in embodiments crystalline Lucerastat: L-Pyroglutamic acid, crystalline Lucerastat: Salicylic acid, crystalline Lucerastat: Fumaric acid, crystalline Lucerastat: Benzoic acid and crystalline Lucerastat: o-Acetylsalicylic acid, solid state form thereof, processes for preparation thereof, and pharmaceutical compositions thereof.

11 Claims, 6 Drawing Sheets

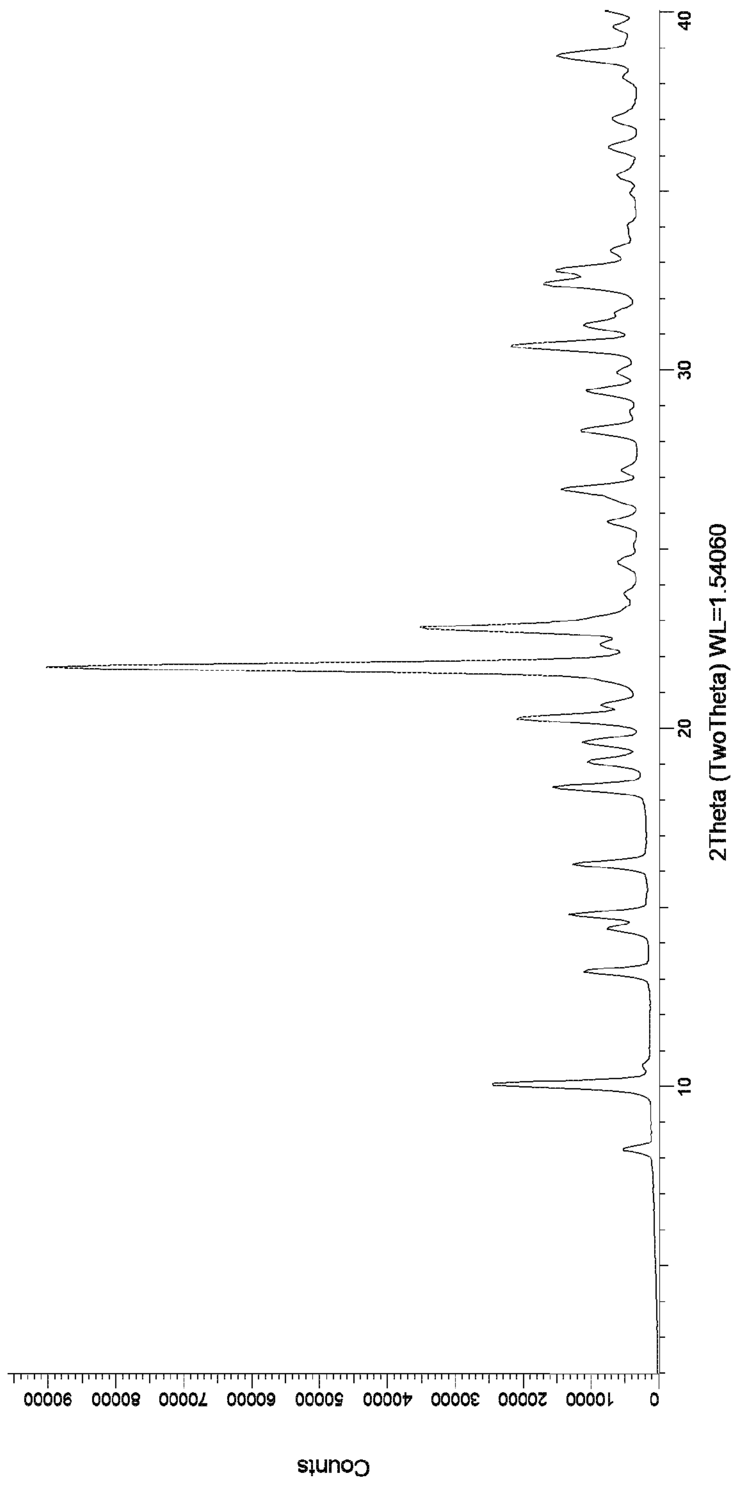
Figure 1: A characteristic X-ray powder diffraction pattern (XRPD) of crystalline Lucerastat: L-pyroglutamic acid (Form LC-1).

Figure 2: A characteristic X-ray powder diffraction pattern (XRPD) of crystalline Lucerastat: Salicylic acid (Form LC-2).
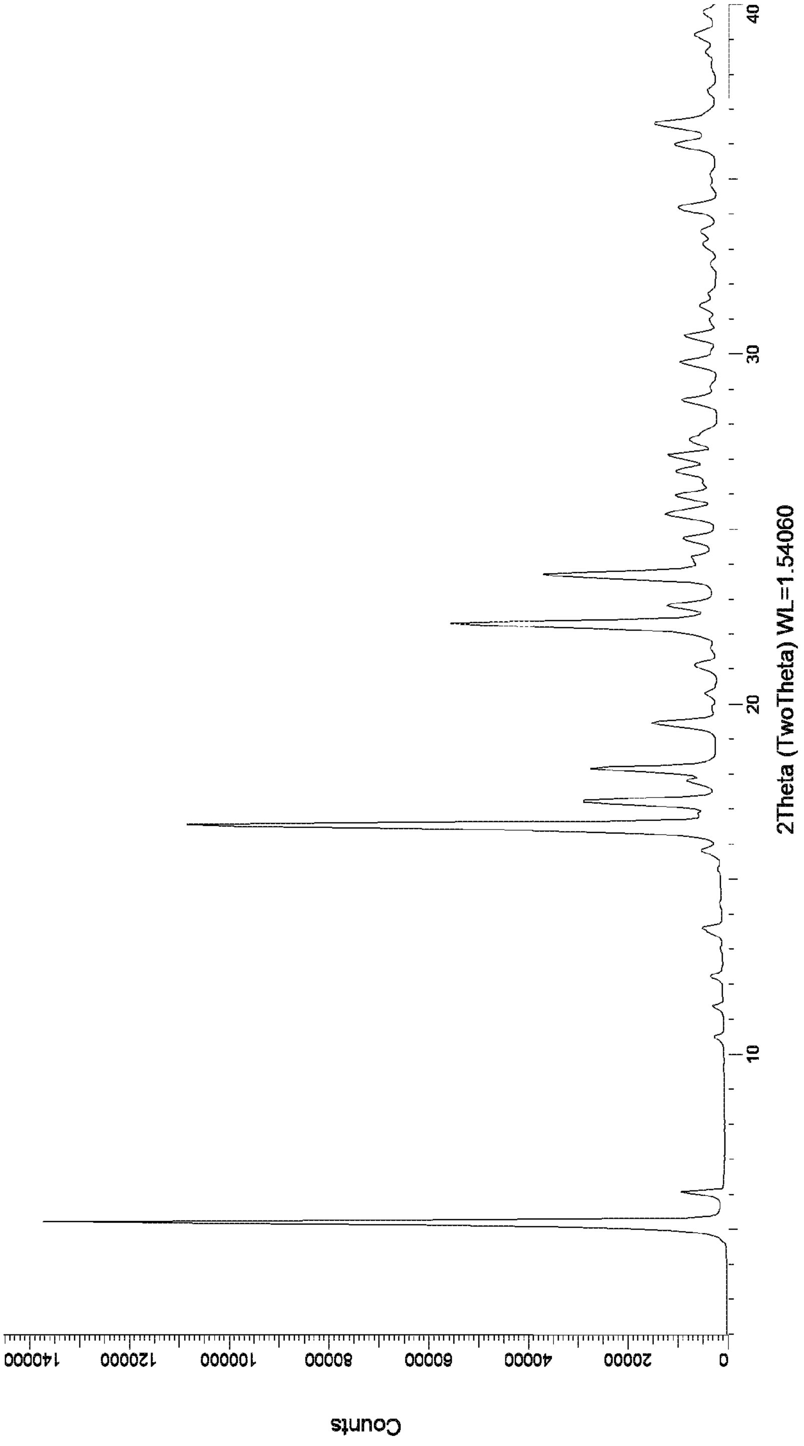

Figure 3: A characteristic X-ray powder diffraction pattern (XRPD) of crystalline Lucerastat: Fumaric acid (Form LC-3).
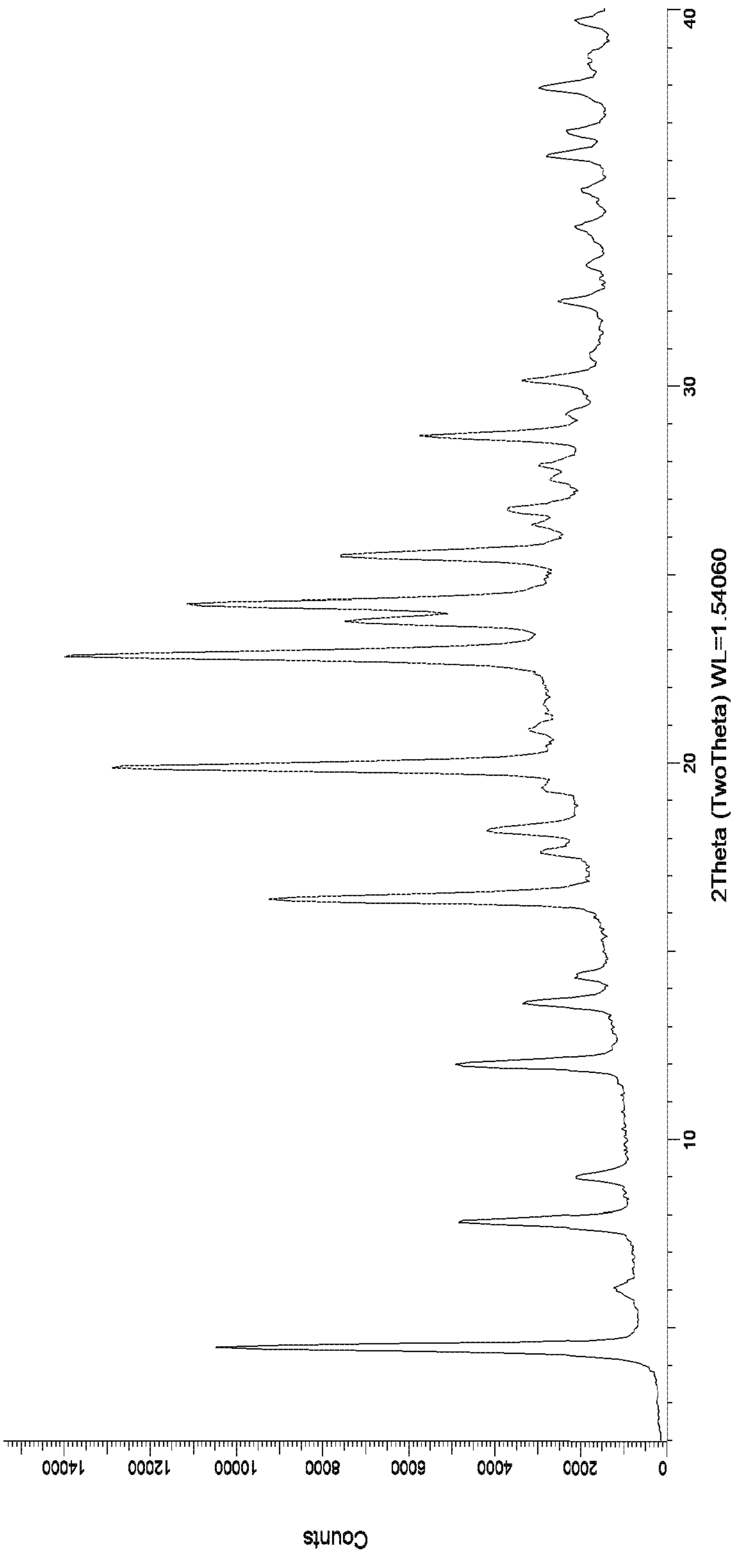

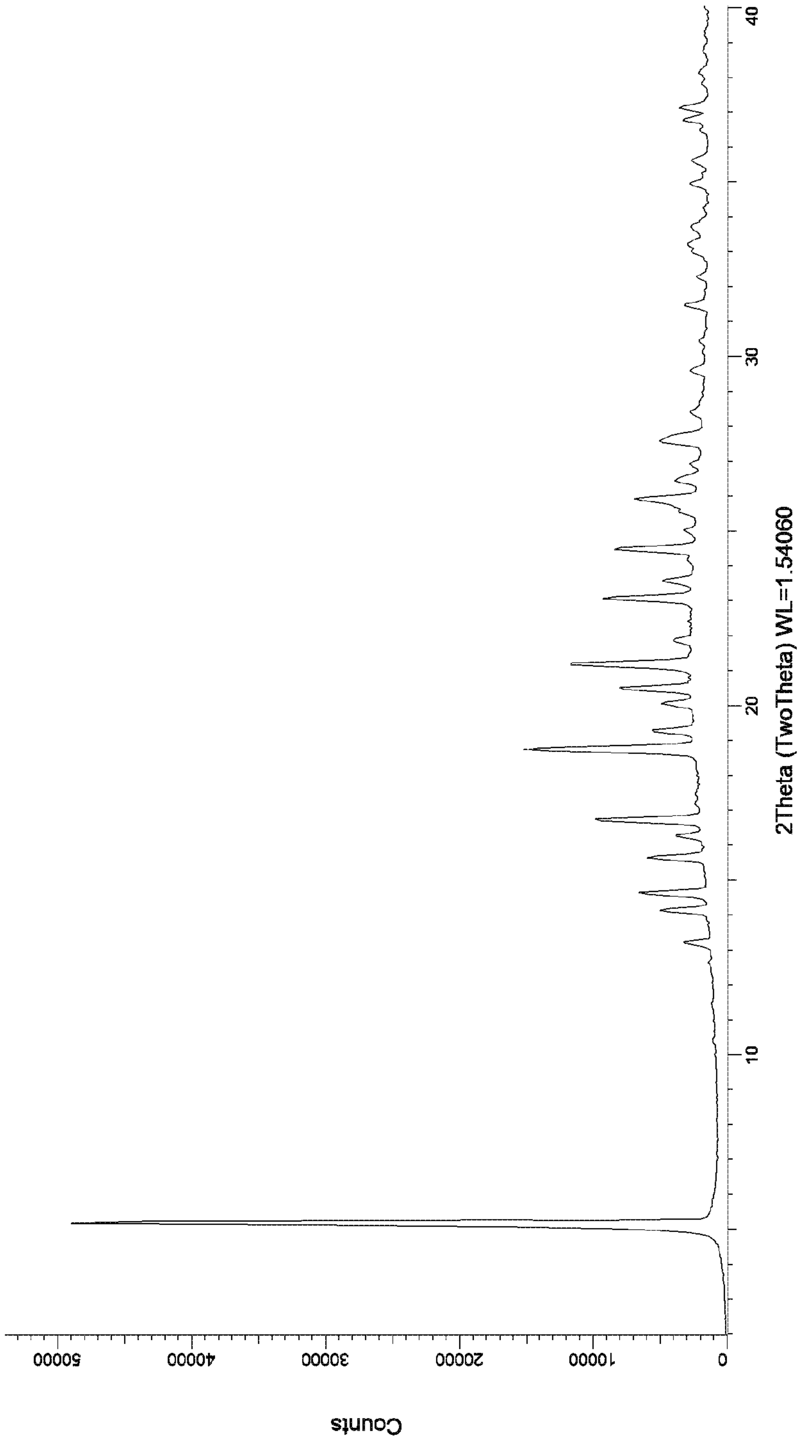
Figure 4. A characteristic XRPD pattern of crystalline Lucerastat: Benzoic acid (Form LC-4).

Figure 5. A characteristic XRPD pattern of crystalline Lucerastat: o- Acetylsalicylic acid (Form LC-5).
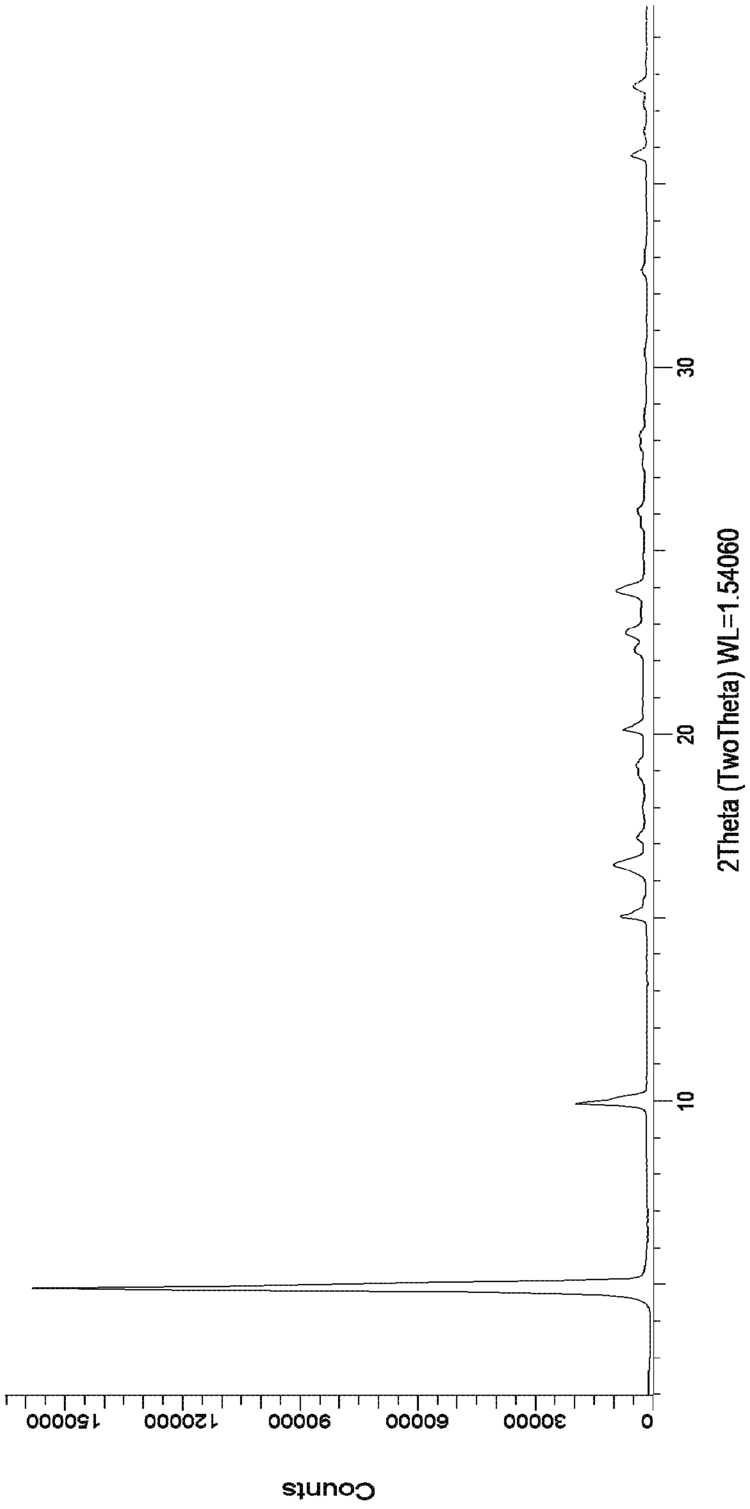

Figure 6. An XRPD pattern of Lucerastat Form 1, as described in WO 2018/220131 (figure 1)
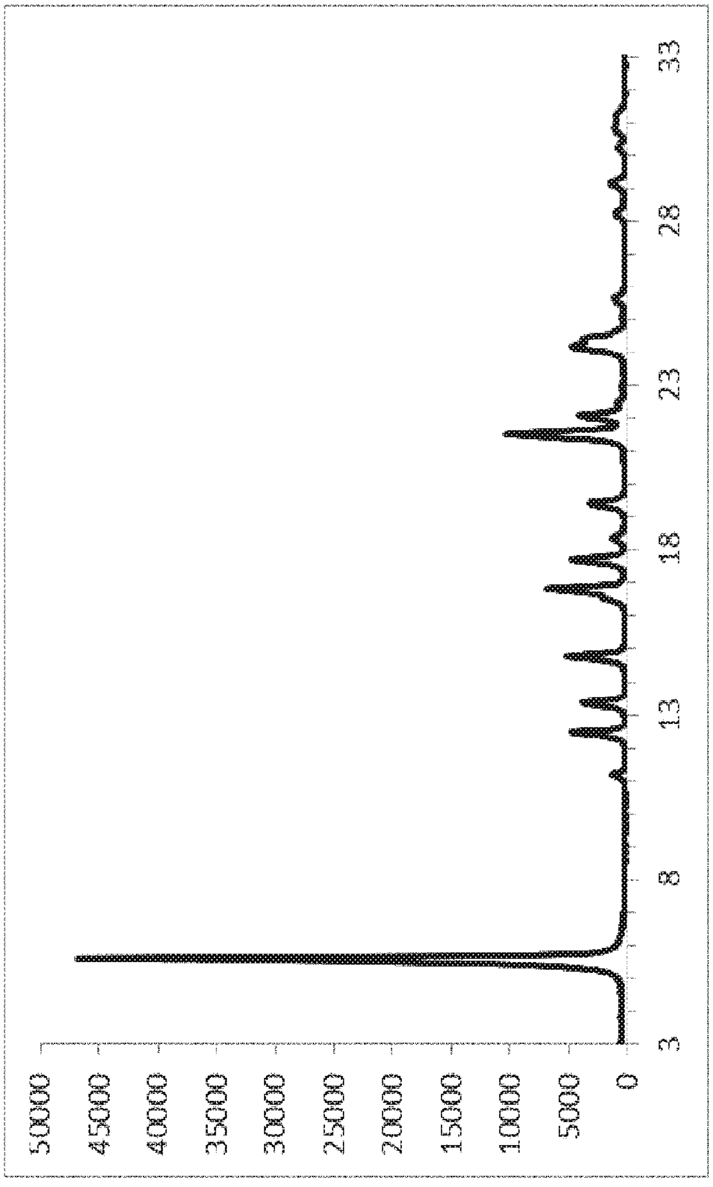

SOLID STATE FORMS OF LUCERASTAT AND PROCESS FOR PREPARATION THEREOF

CROSS REFERENCE TO RELATED APPLICATIONS

This application is a National Stage of, and claims priority to and the benefit of, International Patent Application No. PCT/US2020/052110 filed Sep. 23, 2020, which, in turn, claims the benefit of and priority to, Indian Application No. 201911038702, filed Sep. 25, 2019 and Indian Application No. 201911043541, filed Oct. 25, 2019, the entire disclosures of each of which are incorporated by reference herein.

FIELD OF THE DISCLOSURE

The present disclosure encompasses solid state forms of Lucerastat, in embodiments crystalline Lucerastat: L-Pyroglutamic acid, crystalline Lucerastat: Salicylic acid, crystalline Lucerastat: Fumaric acid, crystalline Lucerastat: Benzoic acid and crystalline Lucerastat: o-Acetylsalicylic acid, solid state form thereof, processes for preparation thereof, and pharmaceutical compositions thereof.

BACKGROUND OF THE DISCLOSURE

Lucerastat, (2R,3S,4R,5S)-1-butyl-2-(hydroxymethyl)piperidine-3,4,5-triol, has the following chemical structure:

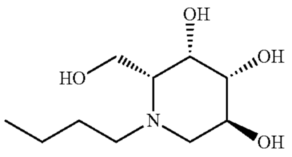

Lucerastat is an orally bioavailable inhibitor of glucosylceramide synthase (GCS) that is in late stage clinical development for treatment of Fabry disease.

The compound is described in U.S. Pat. No. 6,291,657. Lucerastat solid state form is described in the International Publication No. WO 2018/220131.

Polymorphism, the occurrence of different crystalline forms, is a property of some molecules and molecular complexes. A single molecule may give rise to a variety of polymorphs having distinct crystal structures and physical properties like melting point, thermal behaviors (e.g., measured by thermogravimetric analysis ("TGA"), or differential scanning calorimetry ("DSC"), X-ray diffraction (XRD) pattern, infrared absorption fingerprint, and solid state ($^{13}C$) NMR spectrum. One or more of these techniques may be used to distinguish different polymorphic forms of a compound.

Different salts and solid state forms (including solvated forms) of an active pharmaceutical ingredient may possess different properties. Such variations in the properties of different salts and solid state forms and solvates may provide a basis for improving formulation, for example, by facilitating better processing or handling characteristics, changing the dissolution profile in a favorable direction, or improving stability (polymorph as well as chemical stability) and shelf-life. These variations in the properties of different salts and solid state forms may also offer improvements to the final dosage form, for instance, if they serve to improve bioavailability. Different salts and solid state forms and solvates of an active pharmaceutical ingredient may also give rise to a variety of polymorphs or crystalline forms, which may in turn provide additional opportunities to assess variations in the properties and characteristics of a solid active pharmaceutical ingredient.

Discovering new solid state forms and solvates of a pharmaceutical product may yield materials having desirable processing properties, such as ease of handling, ease of processing, storage stability, and ease of purification or as desirable intermediate crystal forms that facilitate conversion to other polymorphic forms. New solid state forms of a pharmaceutically useful compound can also provide an opportunity to improve the performance characteristics of a pharmaceutical product. It enlarges the repertoire of materials that a formulation scientist has available for formulation optimization, for example by providing a product with different properties, including a different crystal habit, higher crystallinity, or polymorphic stability, which may offer better processing or handling characteristics, improved dissolution profile, or improved shelf-life (chemical/physical stability). For at least these reasons, there is a need for additional solid state forms (including solvated forms) of Lucerastat. Furthermore, there is a need for additional solid state forms of Lucerastat: L-Pyroglutamic acid, Lucerastat: Salicylic acid, Lucerastat: Fumaric acid, Lucerastat: Benzoic acid and Lucerastat: o-Acetylsalicylic acid, which offer superior properties without altering the pharmacological properties.

SUMMARY OF THE DISCLOSURE

The present disclosure relates to solid state forms of Lucerastat. More particularly, the present disclosure relates to a salt of Lucerastat in the form of a solid, particular wherein the salt of Lucerastat is an acid addition salt in the form of a solid. The present disclosure encompasses an acid addition salt of Lucerastat which is in the form of an isolated solid. In embodiments, the disclosure relates to a salt of Lucerastat containing less than 10 wt % water, or a salt of Lucerastat which is non-deliquescent, for example, wherein the salt can be isolated as a solid, or particularly wherein the salt is isolated as a solid, and moreover remains solid when exposed to 20-80% relative humidity (RH) for 7 days e.g. at room temperature. In particular, the present disclosure encompasses salts of Lucerastat, including: Lucerastat: L-Pyroglutamic acid, Lucerastat: Salicylic acid, Lucerastat: Fumaric acid, Lucerastat: Benzoic acid and Lucerastat: o-Acetylsalicylic acid and their solid state forms, particularly crystalline forms thereof.

Accordingly, the present disclosure relates to crystalline Lucerastat: L-Pyroglutamic acid, crystalline Lucerastat: Salicylic acid, crystalline Lucerastat: Fumaric acid, crystalline Lucerastat: Benzoic acid and crystalline Lucerastat: o-Acetylsalicylic acid and their solid state forms. The present disclosure also relates to processes for preparation thereof, and pharmaceutical compositions comprising crystalline Lucerastat: L-Pyroglutamic acid, crystalline Lucerastat: Salicylic acid, crystalline Lucerastat: Fumaric acid, crystalline Lucerastat: Benzoic acid and crystalline Lucerastat: o-Acetylsalicylic acid and their solid state forms.

The present disclosure provides crystalline Lucerastat: L-Pyroglutamic acid, crystalline Lucerastat: Salicylic acid, crystalline Lucerastat: Fumaric acid, crystalline Lucerastat: Benzoic acid and crystalline Lucerastat: o-Acetylsalicylic acid and their solid state forms, for use in medicine, including for the treatment of Fabry disease.

The present disclosure also encompasses the use of crystalline Lucerastat: L-Pyroglutamic acid, crystalline Lucerastat: Salicylic acid, crystalline Lucerastat: Fumaric acid, crystalline Lucerastat: Benzoic acid and crystalline Lucerastat: o-Acetylsalicylic acid and their solid state forms for the preparation of pharmaceutical compositions and/or formulations.

In another aspect, the present disclosure provides pharmaceutical compositions comprising crystalline Lucerastat: L-Pyroglutamic acid, crystalline Lucerastat: Salicylic acid, crystalline Lucerastat: Fumaric acid, crystalline Lucerastat: Benzoic acid and crystalline Lucerastat: o-Acetylsalicylic acid and their solid state forms.

The present disclosure includes processes for preparing the above mentioned pharmaceutical compositions. The processes include combining crystalline Lucerastat: L-Pyroglutamic acid, crystalline Lucerastat: Salicylic acid, crystalline Lucerastat: Fumaric acid, crystalline Lucerastat: Benzoic acid and crystalline Lucerastat: o-Acetylsalicylic acid and their solid state forms, with at least one pharmaceutically acceptable excipient.

The crystalline Lucerastat: L-Pyroglutamic acid, crystalline Lucerastat: Salicylic acid, crystalline Lucerastat: Fumaric acid, crystalline Lucerastat: Benzoic acid and crystalline Lucerastat: o-Acetylsalicylic acid and their solid state forms, as defined herein and the pharmaceutical compositions or formulations of crystalline Lucerastat: L-Pyroglutamic acid, crystalline Lucerastat: Salicylic acid, crystalline Lucerastat: Fumaric acid, crystalline Lucerastat: Benzoic acid and crystalline Lucerastat: o-Acetylsalicylic acid and their solid state forms, may be used as medicaments, such as for the treatment of Fabry disease.

The present disclosure also provides methods of treating Fabry disease, by administering a therapeutically effective amount of crystalline Lucerastat: L-Pyroglutamic acid, crystalline Lucerastat: Salicylic acid, crystalline Lucerastat: Fumaric acid, crystalline Lucerastat: Benzoic acid and crystalline Lucerastat: o-Acetylsalicylic acid and their solid state forms, or at least one of the above pharmaceutical compositions, to a subject suffering from Fabry disease, or otherwise in need of the treatment.

The present disclosure also provides uses of Lucerastat: L-Pyroglutamic acid, Lucerastat: Salicylic acid, Lucerastat: Fumaric acid, Lucerastat: Benzoic acid and Lucerastat: o-Acetylsalicylic acid and their solid state forms, or at least one of the above pharmaceutical compositions, for the manufacture of medicaments for treating e.g. Fabry disease.

BRIEF DESCRIPTION OF THE DRAWINGS

FIG. 1 shows a characteristic X-ray powder diffraction pattern (XRPD) of crystalline Lucerastat: L-Pyroglutamic acid (Form LC-1).

FIG. 2 shows a characteristic X-ray powder diffraction pattern (XRPD) of crystalline Lucerastat: Salicylic acid (Form LC-2).

FIG. 3 shows a characteristic X-ray powder diffraction pattern (XRPD) of crystalline Lucerastat: Fumaric acid (Form LC-3).

FIG. 4 shows a characteristic XRPD pattern of crystalline Lucerastat: Benzoic acid (Form LC-4).

FIG. 5 shows a characteristic XRPD pattern of crystalline Lucerastat: o-Acetylsalicylic acid (Form LC-5).

FIG. 6 shows an XRPD pattern of Lucerastat, Form 1, as described in International Publication No. WO 2018/220131 (FIG. 1).

DETAILED DESCRIPTION OF THE DISCLOSURE

The present disclosure encompasses solid state forms of crystalline Lucerastat: L-Pyroglutamic acid, crystalline Lucerastat: Salicylic acid, crystalline Lucerastat: Fumaric acid, crystalline Lucerastat: Benzoic acid and crystalline Lucerastat: o-Acetylsalicylic acid, processes for preparation thereof, and pharmaceutical compositions thereof.

Solid state properties of Lucerastat: L-Pyroglutamic acid, Lucerastat: Salicylic acid, Lucerastat: Fumaric acid, Lucerastat: Benzoic acid and Lucerastat: o-Acetylsalicylic acid, and particularly crystalline Lucerastat: L-Pyroglutamic acid, crystalline Lucerastat: Salicylic acid, crystalline Lucerastat: Fumaric acid, crystalline Lucerastat: Benzoic acid and crystalline Lucerastat: o-Acetylsalicylic acid can be influenced by controlling the conditions under which Lucerastat: L-Pyroglutamic acid, Lucerastat: Salicylic acid, Lucerastat: Fumaric acid, Lucerastat: Benzoic acid and Lucerastat: o-Acetylsalicylic acid, particularly crystalline Lucerastat: L-Pyroglutamic acid, crystalline Lucerastat: Salicylic acid, crystalline Lucerastat: Fumaric acid, crystalline Lucerastat: Benzoic acid and crystalline Lucerastat: o-Acetylsalicylic acid is obtained in solid form.

A solid state form (or polymorph) may be referred to herein as polymorphically pure or as substantially free of any other solid state (or polymorphic) forms. As used herein in this context, the expression "substantially free of any other forms" will be understood to mean that the solid state form contains about 20% (w/w) or less, about 10% (w/w) or less, about 5% (w/w) or less, about 2% (w/w) or less, about 1% (w/w) or less, or about 0% of any other forms of the subject compound as measured, for example, by XRPD. Thus, a crystalline Lucerastat: L-Pyroglutamic acid, crystalline Lucerastat: Salicylic acid, crystalline Lucerastat: Fumaric acid, crystalline Lucerastat: Benzoic acid and crystalline Lucerastat: o-Acetylsalicylic acid described herein as substantially free of any other solid state forms would be understood to contain greater than about 80% (w/w), greater than about 90% (w/w), greater than about 95% (w/w), greater than about 98% (w/w), greater than about 99% (w/w), or about 100% of the subject crystalline Lucerastat: L-Pyroglutamic acid, crystalline Lucerastat: Salicylic acid, crystalline Lucerastat: Fumaric acid, crystalline Lucerastat: Benzoic acid and Lucerastat: o-Acetylsalicylic acid. In some embodiments of the disclosure, the described crystalline Lucerastat: L-Pyroglutamic acid, crystalline Lucerastat: Salicylic acid, crystalline Lucerastat: Fumaric acid, crystalline Lucerastat: Benzoic acid and crystalline Lucerastat: o-Acetylsalicylic acid may contain from about 1% to about 20% (w/w), from about 5% to about 20% (w/w), or from about 5% to about 10% (w/w) of one or more other crystalline polymorph of the same crystalline Lucerastat: L-Pyroglutamic acid, crystalline Lucerastat: Salicylic acid, crystalline Lucerastat: Fumaric acid, crystalline Lucerastat: Benzoic acid and Lucerastat: o-Acetylsalicylic acid.

Depending on which other crystalline polymorphs a comparison is made, the crystalline Lucerastat: L-Pyroglutamic acid, crystalline Lucerastat: Salicylic acid, crystalline Lucerastat: Fumaric acid, crystalline Lucerastat: Benzoic acid and crystalline Lucerastat: o-Acetylsalicylic acid and solid state forms may have advantageous properties selected from at least one of the following: chemical purity, flowability, solubility, dissolution rate, morphology or crystal habit, stability, such as chemical stability as well as thermal and mechanical stability with respect to polymorphic conversion, stability towards dehydration and/or storage stability, low content of residual solvent, a lower degree of hygroscopicity, flowability, and advantageous processing and handling characteristics such as compressibility and bulk density.

A solid state form, such as a crystal form or an amorphous form, may be referred to herein as being characterized by graphical data "as depicted in" or "as substantially depicted in" a Figure. Such data include, for example, powder X-ray diffractograms and solid state NMR spectra. As is well-known in the art, the graphical data potentially provides additional technical information to further define the respective solid state form (a so-called "fingerprint") which cannot necessarily be described by reference to numerical values or peak positions alone. In any event, the skilled person will understand that such graphical representations of data may be subject to small variations, e.g., in peak relative intensities and peak positions due to certain factors such as, but not limited to, variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms. A crystalline Lucerastat: L-pyroglutamic acid, crystalline Lucerastat: Salicylic acid, crystalline Lucerastat: Fumaric acid, crystalline Lucerastat: Benzoic acid and crystalline Lucerastat: o-Acetylsalicylic acid referred to herein as being characterized by graphical data "as depicted in" or "as substantially depicted in" a Figure will thus be understood to include any crystal forms of Lucerastat: L-pyroglutamic acid, Lucerastat: Salicylic acid, Lucerastat: Fumaric acid, Lucerastat: Benzoic acid and Lucerastat: o-Acetylsalicylic acid characterized with the graphical data having such small variations, as are well known to the skilled person, in comparison with the Figure.

As used herein, and unless stated otherwise, the term "anhydrous" in relation to crystalline Lucerastat: L-pyroglutamic acid, crystalline Lucerastat: Salicylic acid, crystalline Lucerastat: Fumaric acid, crystalline Lucerastat: Benzoic acid and crystalline Lucerastat: o-Acetyl Salicylic acid and solid state form thereof, relate to a crystalline form of Lucerastat: L-pyroglutamic acid, Lucerastat: Salicylic acid, Lucerastat: Fumaric acid, Lucerastat: Benzoic acid and Lucerastat: o-Acetylsalicylic acid and solid state form thereof, which does not include any crystalline water (or other solvents) in a defined, stoichiometric amount within the crystal. Moreover, an "anhydrous" form would generally not contain more than 1% (w/w), of either water or organic solvents as measured for example by TGA.

The term "solvate," as used herein and unless indicated otherwise, refers to a crystal form that incorporates a solvent in the crystal structure. When the solvent is water, the solvate is often referred to as a "hydrate." The solvent in a solvate may be present in either a stoichiometric or in a non-stoichiometric amount.

As used herein, crystalline Lucerastat: L-pyroglutamic acid is a distinct molecular species. In another embodiment crystalline Lucerastat: L-pyroglutamic acid may be a salt.

In a preferred embodiment the molar ratio between the active pharmaceutical ingredient (Lucerastat) and the coformer (L-Pyroglutamic acid is between 1:1.5 and 1.5:1, preferably between 1:1.25 and 1.25:1, most preferably about 1:1. Thus, preferred embodiments of the disclosure relate to Lucerastat: L-Pyroglutamic acid, wherein the molar ratio of the Lucerastat to L-Pyroglutamic acid is between 1:1.5 and 1.5:1, preferably between 1:1.25 and 1.25:1, most preferably about 1:1.

As used herein, crystalline Lucerastat: Salicylic acid is a distinct molecular species. In another embodiment crystalline Lucerastat: Salicylic acid may be a salt.

In a preferred embodiment the molar ratio between the active pharmaceutical ingredient (Lucerastat) and the coformer (Salicylic acid) is between 1:1.5 and 1.5:1, preferably between 1:1.25 and 1.25:1, most preferably about 1:1. Thus, preferred embodiments of the disclosure relate to Lucerastat: Salicylic acid wherein the molar ratio of Lucerastat to Salicylic acid is between 1:1.5 and 1.5:1, preferably between 1:1.25 and 1.25:1, most preferably about 1:1.

As used herein, crystalline Lucerastat: Fumaric acid is a distinct molecular species. In another embodiment crystalline Lucerastat: Fumaric acid may be a salt.

In a preferred embodiment the molar ratio between the active pharmaceutical ingredient (Lucerastat) and the coformer (Fumaric acid) is between 1:1.5 and 1.5:1, preferably between 1:1.25 and 1.25:1, most preferably about 1:1.

As used herein, crystalline Lucerastat: Benzoic acid is a distinct molecular species. In another embodiment crystalline Lucerastat: Benzoic acid may be a salt.

In a preferred embodiment the molar ratio between the active pharmaceutical ingredient (Lucerastat) and the coformer (Benzoic acid) is between 1:1.5 and 1.5:1, preferably between 1:1.25 and 1.25:1, most preferably about 1:1. Thus, preferred embodiments of the disclosure relate to Lucerastat: Benzoic acid wherein the molar ratio of Lucerastat to Benzoic acid is between 1:1.5 and 1.5:1, preferably between 1:1.25 and 1.25:1, most preferably about 1:1.

As used herein, crystalline Lucerastat: o-Acetylsalicylic acid is a distinct molecular species. In another embodiment crystalline Lucerastat: o-Acetylsalicylic acid may be a salt.

In a preferred embodiment the molar ratio between the active pharmaceutical ingredient (Lucerastat) and the coformer (o-Acetylsalicylic acid) is between 1:1.5 and 1.5:1, preferably between 1:1.25 and 1.25:1, most preferably about 1:1. Thus, preferred embodiments of the disclosure relate to Lucerastat: o-Acetylsalicylic acid wherein the molar ratio of Lucerastat to o-Acetylsalicylic acid is between 1:1.5 and 1.5:1, preferably between 1:1.25 and 1.25:1, most preferably about 1:1.

As used therein the term "Lucerastat Form 1" relates to a crystalline form having an XRPD pattern shown herein in FIG. 6, as described in International Publication No. WO 2018/220131 (FIG. 1 therein). For example, as defined in International Publication No. WO 2018/220131, Lucerastat Form 1 has an XRPD pattern with characteristic peaks at: 5.6, 12.4, 13.4, 14.8, 16.8, 17.7, 19.4, 21.5, 22.1 and 24.2 degrees 2-theta ±0.2 degrees 2-theta.

As used herein, the term "isolated" in reference to crystalline Lucerastat: L-Pyroglutamic acid, crystalline Lucerastat: Salicylic acid, crystalline Lucerastat: Fumaric acid, crystalline Lucerastat: Benzoic acid and crystalline Lucerastat: o-Acetylsalicylic acid of the present disclosure corresponds to crystalline Lucerastat: L-Pyroglutamic acid, crystalline Lucerastat: Salicylic acid, crystalline Lucerastat: Fumaric acid, crystalline Lucerastat: Benzoic acid and crystalline Lucerastat: o-Acetylsalicylic acid that is physically separated from the reaction mixture in which it is formed.

As used herein, unless stated otherwise, the XRPD measurements are taken using copper Kα radiation wavelength 1.54187 Å. XRPD peaks reported herein are measured using CuK α radiation, λ=1.54187 Å, typically at a temperature of 25±3° C.

A thing, e.g., a reaction mixture, may be characterized herein as being at, or allowed to come to "room temperature" or "ambient temperature", often abbreviated as "RT." This means that the temperature of the thing is close to, or the same as, that of the space, e.g., the room or fume hood, in which the thing is located. Typically, room temperature is from about 20° C. to about 30° C., or about 22° C. to about 27° C., or about 25° C.

The amount of solvent employed in a chemical process, e.g., a reaction or crystallization, may be referred to herein as a number of "volumes" or "vol" or "V." For example, a material may be referred to as being suspended in 10 volumes (or 10 vol or 10V) of a solvent. In this context, this expression would be understood to mean milliliters of the solvent per gram of the material being suspended, such that suspending a 5 grams of a material in 10 volumes of a solvent means that the solvent is used in an amount of 10 milliliters of the solvent per gram of the material that is being suspended or, in this example, 50 mL of the solvent. In another context, the term "v/v" may be used to indicate the number of volumes of a solvent that are added to a liquid mixture based on the volume of that mixture. For example, adding solvent X (1.5 v/v) to a 100 ml reaction mixture would indicate that 150 mL of solvent X was added.

A process or step may be referred to herein as being carried out "overnight." This refers to a time interval, e.g., for the process or step, that spans the time during the night, when that process or step may not be actively observed. This time interval is from about 8 to about 20 hours, or about 10-18 hours, in some cases about 16 hours.

As used herein, the term "reduced pressure" refers to a pressure that is less than atmospheric pressure. For example, reduced pressure is about 10 mbar to about 50 mbar.

As used herein and unless indicated otherwise, the term "ambient conditions" refer to atmospheric pressure and a temperature of 22-24° C.

The present disclosure encompasses Lucerastat: L-pyroglutamic acid. The present disclosure includes crystalline Lucerastat: L-Pyroglutamic acid, designated Form LC-1. The crystalline Form LC-1 of Lucerastat: L-pyroglutamic acid may be characterized by data selected from one or more of the following: an X-ray powder diffraction pattern substantially as depicted in FIG. 1; an X-ray powder diffraction pattern having peaks at 10.1, 13.3, 16.3, 20.3 and 30.7 degrees 2-theta ±0.2 degrees 2-theta; and combinations of these data.

Crystalline Form LC-1 of Lucerastat: L-pyroglutamic acid may be further characterized by an X-ray powder diffraction pattern having peaks at 10.1, 13.3, 16.3, 20.3 and 30.7 degrees 2-theta ±0.2 degrees 2-theta, and also having any one, two, three, four or five additional peaks selected from 8.3, 14.5, 18.4, 21.8 and 22.9 degrees 2-theta ±0.2 degrees 2-theta.

Crystalline Lucerastat: L-pyroglutamic acid Form LC-1 may alternatively be characterized by an XRPD pattern having peaks at 8.3, 10.1, 13.3, 14.5, 16.3, 18.4, 20.3, 21.8, 22.9 and 30.7 degrees 2-theta ±0.2 degrees 2-theta.

Crystalline Form LC-1 of Lucerastat: L-pyroglutamic acid may be characterized by each of the above characteristics alone/or by all possible combinations, e.g., an XRPD pattern having peaks at 10.1, 13.3, 16.3, 20.3 and 30.7 degrees 2-theta ±0.2 degrees 2-theta; an XRPD pattern as depicted in FIG. 1, and combinations thereof.

In another embodiment crystalline form LC-1 of Lucerastat: L-pyroglutamic acid may be a salt.

In one embodiment of the present disclosure, crystalline Lucerastat: L-pyroglutamic acid Form LC-1 is polymorphically pure.

In one embodiment of the present disclosure, crystalline Form LC-1 of Lucerastat: L-pyroglutamic acid is isolated.

Crystalline Form LC1 of Lucerastat: L-pyroglutamic acid may be characterized as anhydrous form. In another embodiment Crystalline Lucerastat: L-pyroglutamic acid form LC-1 may be characterized as a hydrate. In certain embodiments, crystalline Lucerastat: L-pyroglutamic acid Form LC-1 may contain less than 3% (w/w) or less than 2% (w/w) water and/or any other solvents, in another embodiment less than 1.5% (w/w) water or any other solvents. In other embodiments, crystalline Lucerastat: L-pyroglutamic acid Form LC-1 may contain: from 0.5 to 2.5% (w/w), from 0.8 to 2% (w/w), from 0.9 to 1.5% (w/w), from 1.0 to 1.4% (w/w), or about 1.2% (w/w) water.

Crystalline Lucerastat: L-pyroglutamic acid according to any of the embodiments described herein may contain: not more than about 10% (w/w), not more than about 9% (w/w), or not more than about 8% (w/w) water when exposed to high relative humidity, for example, when exposed up to 95% RH at room temperature (as measured by DVS).

Crystalline Lucerastat: L-pyroglutamic acid according to any of the embodiments described herein may contain: 0.5 wt % to 5 wt % water, 0.8 wt % to 4 wt % water, 1.0 wt % to 3.5 wt %, 1.0 wt % to 3 wt % water, about 1.1 to about 2 wt % water, or about 1.1 to about 1.5 wt % water, after storage at 20-80% relative humidity (RH) for 7 days at room temperature.

As described above, depending on which other solid state it is compared with, crystalline Lucerastat: L-pyroglutamic acid Form LC-1 according to the present disclosure may have one or more advantageous properties as described above. Crystalline Lucerastat: L-pyroglutamic acid according to any of the described embodiments is stable, and remains solid, for example, when exposed 20-80% RH for 7 days at room temperature. For example, crystalline Lucerastat: L-pyroglutamic acid Form LC-1 is polymorphically stable and in particular does not deliquesce when exposed to 20-80% RH for 7 days at room temperature. Furthermore, crystalline Lucerastat: L-pyroglutamic acid Form LC-1 shows long term stability at 2-8° C. for at least 1 year.

The above crystalline polymorph can be used to prepare other crystalline polymorphs of Lucerastat: L-pyroglutamic acid.

The present disclosure encompasses Lucerastat: Salicylic acid. The present disclosure includes crystalline Lucerastat: Salicylic acid designated Form LC-2. The crystalline Form LC-2 of Lucerastat: Salicylic acid may be characterized by data selected from one or more of the following: an X-ray powder diffraction pattern substantially as depicted in FIG. 2; an X-ray powder diffraction pattern having peaks at 5.2, 16.6, 18.2, 22.3 and 23.7 degrees 2-theta ±0.2 degrees 2-theta; and combinations of these data.

Crystalline Form LC-2 of Lucerastat: Salicylic acid may be further characterized by an X-ray powder diffraction pattern having peaks at 5.2, 16.6, 18.2, 22.3 and 23.7 degrees 2-theta ±0.2 degrees 2-theta, and also having any one, two, three, four or five additional peaks selected from 17.3, 19.5, 25.5, 22.9 and 34.2 degrees 2-theta ±0.2 degrees 2-theta.

Crystalline Lucerastat: Salicylic acid Form LC-2 may alternatively be characterized by an XRPD pattern having peaks at 5.2, 16.6, 17.3, 18.2, 19.5, 22.3, 22.9, 23.7, 25.5 and 34.2 degrees 2-theta ±0.2 degrees 2-theta.

Crystalline Form LC-2 of Lucerastat: Salicylic acid may be characterized by each of the above characteristics alone/ or by all possible combinations, e.g., an XRPD pattern having peaks at 5.2, 16.6, 18.2, 22.3 and 23.7 degrees 2-theta ±0.2 degrees 2-theta; an XRPD pattern as depicted in FIG. 2, and combinations thereof.

In another embodiment crystalline form LC-2 of Lucerastat: Salicylic acid may be a salt.

In one embodiment of the present disclosure, crystalline Lucerastat: Salicylic acid Form LC-2 is polymorphically pure.

In one embodiment of the present disclosure, crystalline Form LC-2 of Lucerastat: Salicylic acid is isolated.

Crystalline Form LC-2 of Lucerastat: Salicylic acid may be monohydrate. In embodiments, crystalline Form LC-2 of Lucerastat: Salicylic acid contains about 3-7% (w/w), about 4-6% (w/w) or about 4.5-5.5% (w/w), preferably about 5% (w/w) water or any other solvents. In other embodiments, crystalline Form LC-2 of Lucerastat: Salicylic acid may contain from: about 3-7% (w/w), about 4-6% (w/w) or about 4.5-5.5% (w/w), preferably about 5% (w/w) water.

As described above, depending on which other solid state it is compared with, crystalline Lucerastat: Salicylic acid Form LC-2 according to the present disclosure may have one or more advantageous properties as described above. Crystalline Lucerastat: Salicylic acid according to any of the described embodiments is stable, and remains solid, for example, when exposed 20-80% RH for 7 days at room temperature. For example, crystalline Lucerastat: Salicylic acid Form LC-2 is polymorphically stable and does not deliquesce when exposed to 20-80% RH for 7 days at room temperature. Furthermore, crystalline Lucerastat: Salicylic acid Form LC-2 shows long term stability at 2-8° C. for at least 1 year.

Crystalline Lucerastat: Salicylic acid as described in any of the embodiments herein may contain less than 7 wt %, or less than 6 wt % water, when exposed to high relative humidity, for example, when exposed to 95% RH at room temperature (as measured by DVS).

Crystalline Lucerastat: Salicylic acid as described in any of the embodiments herein may contain from: 3 wt % to 7 wt %, 3 wt % to 6 wt % water, 4 wt % to 6 wt %, 4.5 wt % to 5.5 wt %, 4 wt % to 5.5 wt % water, 4.5 to 5 wt %, or about 5 wt % water, after storage at 20-80% relative humidity (RH) for 7 days at room temperature.

The above crystalline polymorph can be used to prepare other crystalline polymorphs of Lucerastat: Salicylic acid.

The present disclosure includes crystalline Lucerastat: Fumaric acid designated Form LC-3. The crystalline Form LC-3 of Lucerastat: Fumaric acid may be characterized by data selected from one or more of the following: an X-ray powder diffraction pattern substantially as depicted in FIG. 3; an X-ray powder diffraction pattern having peaks at 4.6, 7.9, 12.1, 20.0 and 23.0 degrees 2-theta ±0.2 degrees 2-theta; and combinations of these data.

Crystalline Form LC-3 of Lucerastat: Fumaric acid may be further characterized by an X-ray powder diffraction pattern having peaks at 4.6, 7.9, 12.1, 20.0 and 23.0 degrees 2-theta ±0.2 degrees 2-theta, and also having any one, two, three, four or five additional peaks selected from 9.1, 16.5, 18.3, 23.9 and 25.6 degrees 2-theta ±0.2 degrees 2-theta.

Crystalline Lucerastat: Fumaric acid Form LC-3 may alternatively be characterized by an XRPD pattern having peaks at 4.6, 7.9, 9.1, 12.1, 16.5, 18.3, 20.0, 23.0, 23.9 and 25.6 degrees 2-theta ±0.2 degrees 2-theta.

Crystalline Form LC-3 of Lucerastat: Fumaric acid may be characterized by each of the above characteristics alone/or by all possible combinations, e.g., an XRPD pattern having peaks at 4.6, 7.9, 12.1, 20.0 and 23.0 degrees 2-theta ±0.2 degrees 2-theta; an XRPD pattern as depicted in FIG. 3, and combinations thereof.

In another embodiment crystalline form LC-3 of Lucerastat: Fumaric acid may be a salt.

In one embodiment of the present disclosure, crystalline Lucerastat: Fumaric acid Form LC-3 is polymorphically pure.

In one embodiment of the present disclosure, crystalline Form LC-3 of Lucerastat: Fumaric acid is isolated.

Crystalline Form LC-3 of Lucerastat: Fumaric acid may be dihydrate, preferably wherein contains 8% to about 13% of water, preferably 9% to about 12%, more preferably 11%.

The above crystalline polymorph can be used to prepare other crystalline polymorphs of Lucerastat: Fumaric acid.

The present disclosure includes crystalline Lucerastat: Benzoic acid designated Form LC-4. The crystalline Form LC-4 of Lucerastat: Benzoic acid may be characterized by data selected from one or more of the following: an X-ray powder diffraction pattern substantially as depicted in FIG. 4; an X-ray powder diffraction pattern having peaks at 5.3, 16.8, 18.9, 21.3 and 23.2 degrees 2-theta ±0.2 degrees 2-theta; and combinations of these data.

Crystalline Form LC-4 of Lucerastat: Benzoic acid may be further characterized by an X-ray powder diffraction pattern having peaks at 5.3, 16.8, 18.9, 21.3 and 23.2 degrees 2-theta ±0.2 degrees 2-theta, and also having any one, two, three or four additional peaks selected from 14.3, 14.7, 15.8 and 20.6 degrees 2-theta ±0.2 degrees 2-theta.

Crystalline Lucerastat: Benzoic acid Form LC-4 may alternatively be characterized by an XRPD pattern having peaks at 5.3, 14.3, 14.7, 15.8, 16.8, 18.9, 20.6, 21.3 and 23.2 degrees 2-theta ±0.2 degrees 2-theta.

Crystalline Form LC-4 of Lucerastat: Benzoic acid may be characterized by each of the above characteristics alone/or by all possible combinations, e.g., an XRPD pattern having peaks at 5.3, 16.8, 18.9, 21.3 and 23.2 degrees 2-theta ±0.2 degrees 2-theta; an XRPD pattern as depicted in FIG. 4, and combinations thereof.

In another embodiment crystalline form LC-4 of Lucerastat: Benzoic acid may be a salt.

In one embodiment of the present disclosure, crystalline Lucerastat: Benzoic acid Form LC-4 is polymorphically pure.

In one embodiment of the present disclosure, crystalline Form LC-4 of Lucerastat: Benzoic acid is isolated.

The above crystalline polymorph can be used to prepare other crystalline polymorphs of Lucerastat: Benzoic acid.

The present disclosure includes crystalline Lucerastat: o-Acetylsalicylic acid designated Form LC-5. The crystalline Form LC-5 of Lucerastat: o-Acetylsalicylic acid may be characterized by data selected from one or more of the following: an X-ray powder diffraction pattern substantially as depicted in FIG. 5; an X-ray powder diffraction pattern having peaks at 4.9, 10.0, 15.0, 16.5 and 20.2 degrees 2-theta ±0.2 degrees 2-theta; and combinations of these data.

Crystalline Form LC-5 of Lucerastat: o-Acetylsalicylic acid may be further characterized by an X-ray powder diffraction pattern having peaks at 4.9, 10.0, 15.0, 16.5 and 20.2 degrees 2-theta ±0.2 degrees 2-theta, and also having any one, two, three or four additional peaks selected from 22.8, 23.9, 35.8 and 37.7 degrees 2-theta ±0.2 degrees 2-theta.

Crystalline Lucerastat: o-Acetylsalicylic acid Form LC-5 may alternatively be characterized by an XRPD pattern having peaks at 4.9, 10.0, 15.0, 16.5, 20.2, 22.8, 23.9, 35.8 and 37.7 degrees 2-theta ±0.2 degrees 2-theta.

Crystalline Form LC-5 of Lucerastat: o-Acetylsalicylic acid may be characterized by each of the above characteristics alone/or by all possible combinations, e.g., an XRPD pattern having peaks at 4.9, 10.0, 15.0, 16.5 and 20.2 degrees 2-theta ±0.2 degrees 2-theta; an XRPD pattern as depicted in FIG. 5, and combinations thereof.

In another embodiment crystalline form LC-5 of Lucerastat: o-Acetyl Salicylic acid may be a salt.

In one embodiment of the present disclosure, crystalline Lucerastat: o-Acetyl Salicylic acid Form LC-5 is polymorphically pure.

In one embodiment of the present disclosure, crystalline Form LC-5 of Lucerastat: o-Acetylsalicylic acid is isolated.

The above crystalline polymorph can be used to prepare other crystalline polymorphs of Lucerastat: o-Acetylsalicylic acid.

The present disclosure provides the above described Lucerastat: L-pyroglutamic acid, Lucerastat: Salicylic acid, Lucerastat: Fumaric acid, Lucerastat: Benzoic acid and Lucerastat: o-Acetylsalicylic acid for use in the preparation of pharmaceutical compositions.

The present disclosure provides the above described crystalline polymorph of Lucerastat: L-pyroglutamic acid, crystalline Lucerastat: Salicylic acid, crystalline Lucerastat: Fumaric acid, crystalline Lucerastat: Benzoic acid and crystalline Lucerastat: o-Acetylsalicylic acid for use in the preparation of pharmaceutical compositions comprising crystalline Lucerastat: L-pyroglutamic acid, crystalline Lucerastat: Salicylic acid, crystalline Lucerastat: Fumaric acid, crystalline Lucerastat: Benzoic acid and crystalline Lucerastat: o-Acetylsalicylic acid and/or their solid state forms.

The present disclosure provides the above described Lucerastat: L-pyroglutamic acid, Lucerastat: Salicylic acid, Lucerastat: Fumaric acid, Lucerastat: Benzoic acid and Lucerastat: o-Acetylsalicylic acid for the preparation of pharmaceutical compositions.

The present disclosure also encompasses the use of crystalline Lucerastat: L-pyroglutamic acid, crystalline Lucerastat: Salicylic acid, crystalline Lucerastat: Fumaric acid, crystalline Lucerastat: Benzoic acid and crystalline Lucerastat: o-Acetylsalicylic acid of the present disclosure for the preparation of pharmaceutical compositions of crystalline Lucerastat: L-pyroglutamic acid, crystalline Lucerastat: Salicylic acid, crystalline Lucerastat: Fumaric acid, crystalline Lucerastat: Benzoic acid and crystalline Lucerastat: o-Acetylsalicylic acid, and/or their solid state forms.

The present disclosure provides a process for preparing the above mentioned pharmaceutical compositions comprising combining the above described Lucerastat: L-pyroglutamic acid, Lucerastat: Salicylic acid, Lucerastat: Fumaric acid, Lucerastat: Benzoic acid and Lucerastat: o-Acetylsalicylic acid with at least one pharmaceutically acceptable excipient.

The present disclosure includes processes for preparing the above mentioned pharmaceutical compositions. The processes include combining crystalline Lucerastat: L-pyroglutamic acid, crystalline Lucerastat: Salicylic acid, crystalline Lucerastat: Fumaric acid, crystalline Lucerastat: Benzoic acid and crystalline Lucerastat: o-Acetylsalicylic acid of the present disclosure with at least one pharmaceutically acceptable excipient.

The present disclosure encompasses pharmaceutical combinations or formulations of Lucerastat: L-pyroglutamic acid, Lucerastat: Salicylic acid, Lucerastat: Fumaric acid, Lucerastat: Benzoic acid and Lucerastat: o-Acetylsalicylic acid of the present disclosure.

The present disclosure encompasses pharmaceutical combinations or formulations of crystalline Lucerastat: L-pyroglutamic acid, crystalline Lucerastat: Salicylic acid, crystalline Lucerastat: Fumaric acid, crystalline Lucerastat: Benzoic acid and crystalline Lucerastat: o-Acetylsalicylic acid of the present disclosure. In addition to the active ingredient, the pharmaceutical formulations of the present disclosure can contain one or more excipients.

The present disclosure encompasses processes to prepare said pharmaceutical formulations of Lucerastat: L-pyroglutamic acid, crystalline Lucerastat: Salicylic acid, Lucerastat: Fumaric acid, Lucerastat: Benzoic acid and Lucerastat: o-Acetylsalicylic acid comprising combining the described solid state forms with at least one pharmaceutically acceptable excipient.

The present disclosure encompasses processes to prepare said pharmaceutical formulations of crystalline Lucerastat: L-pyroglutamic acid, crystalline Lucerastat: Salicylic acid, crystalline Lucerastat: Fumaric acid, crystalline Lucerastat: Benzoic acid and crystalline Lucerastat: o-Acetylsalicylic acid comprising combining the described solid state forms of crystalline Lucerastat: L-pyroglutamic acid, crystalline Lucerastat: Salicylic acid, crystalline Lucerastat: Fumaric acid, crystalline Lucerastat: Benzoic acid and crystalline Lucerastat: o-Acetylsalicylic acid and at least one pharmaceutically acceptable excipient. Excipients are added to the formulation for a variety of purposes.

Diluents increase the bulk of a solid pharmaceutical composition, and can make a pharmaceutical dosage form containing the composition easier for the patient and caregiver to handle. Diluents for solid compositions include, for example, microcrystalline cellulose (e.g. Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol, and talc.

Solid pharmaceutical compositions that are compacted into a dosage form, such as a tablet, can include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate, and starch.

The dissolution rate of a compacted solid pharmaceutical composition in the patient's stomach can be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®), and starch.

Glidants can be added to improve the flowability of a non-compacted solid composition and to improve the accuracy of dosing. Excipients that can function as glidants include colloidal silicon dioxide, magnesium trisilicate, powdered cellulose, starch, talc, and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

Flavoring agents and flavor enhancers make the dosage form more palatable to the patient. Common flavoring agents and flavor enhancers for pharmaceutical products that can be included in the composition of the present disclosure include maltol, vanillin, ethyl vanillin, menthol, citric acid, fumaric acid, ethyl maltol, and tartaric acid.

Solid and liquid compositions can also be dyed using any pharmaceutically acceptable colorant to improve their appearance and/or facilitate patient identification of the product and unit dosage level.

In liquid pharmaceutical compositions of the present invention, crystalline Lucerastat: L-pyroglutamic acid, crystalline Lucerastat: Salicylic acid, crystalline Lucerastat: Fumaric acid, crystalline Lucerastat: Benzoic acid and crystalline Lucerastat: o-Acetylsalicylic acid and any other solid excipients can be dissolved or suspended in a liquid carrier such as water, vegetable oil, alcohol, polyethylene glycol, propylene glycol, or glycerin.

Liquid pharmaceutical compositions can contain emulsifying agents to disperse uniformly throughout the composition an active ingredient or other excipient that is not soluble in the liquid carrier. Emulsifying agents that can be useful in liquid compositions of the present invention include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions of the present invention can also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, xanthan gum and combinations thereof.

Sweetening agents such as sorbitol, saccharin, sodium saccharin, sucrose, aspartame, fructose, mannitol, and invert sugar can be added to improve the taste.

Preservatives and chelating agents such as alcohol, sodium benzoate, butylated hydroxyl toluene, butylated hydroxyanisole, and ethylenediamine tetraacetic acid can be added at levels safe for ingestion to improve storage stability.

According to the present disclosure, a liquid composition can also contain a buffer such as gluconic acid, lactic acid, citric acid, or acetic acid, sodium gluconate, sodium lactate, sodium citrate, or sodium acetate. Selection of excipients and the amounts used can be readily determined by the formulation scientist based upon experience and consideration of standard procedures and reference works in the field.

The solid compositions of the present disclosure include powders, granulates, aggregates, and compacted compositions. The dosages include dosages suitable for oral, buccal, rectal, parenteral (including subcutaneous, intramuscular, and intravenous), inhalant, and ophthalmic administration. Although the most suitable administration in any given case will depend on the nature and severity of the condition being treated, in embodiments the route of administration is oral. The dosages can be conveniently presented in unit dosage form and prepared by any of the methods well-known in the pharmaceutical arts.

Dosage forms include solid dosage forms like tablets, powders, capsules, suppositories, sachets, troches, and lozenges, as well as liquid syrups, suspensions, and elixirs.

The dosage form of the present disclosure can be a capsule containing the composition, such as a powdered or granulated solid composition of the disclosure, within either a hard or soft shell. The shell can be made from gelatin and optionally contain a plasticizer such as glycerin and/or sorbitol, an opacifying agent and/or colorant.

The active ingredient and excipients can be formulated into compositions and dosage forms according to methods known in the art.

A composition for tableting or capsule filling can be prepared by wet granulation. In wet granulation, some or all of the active ingredients and excipients in powder form are blended and then further mixed in the presence of a liquid, typically water, that causes the powders to clump into granules. The granulate is screened and/or milled, dried, and then screened and/or milled to the desired particle size. The granulate can then be tableted, or other excipients can be added prior to tableting, such as a glidant and/or a lubricant.

A tableting composition can be prepared conventionally by dry blending. For example, the blended composition of the actives and excipients can be compacted into a slug or a sheet and then comminuted into compacted granules. The compacted granules can subsequently be compressed into a tablet.

As an alternative to dry granulation, a blended composition can be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate, and colloidal silica. The proper use of these and other excipients in direct compression tableting is known to those in the art with experience and skill in particular formulation challenges of direct compression tableting.

A capsule filling of the present disclosure can include any of the aforementioned blends and granulates that were described with reference to tableting, but they are not subjected to a final tableting step.

A pharmaceutical formulation of crystalline Lucerastat: L-pyroglutamic acid, crystalline Lucerastat: Salicylic acid, crystalline Lucerastat: Fumaric acid, crystalline Lucerastat: Benzoic acid and crystalline Lucerastat: o-Acetylsalicylic acid, can be administered. Crystalline Lucerastat: L-pyroglutamic acid, crystalline Lucerastat: Salicylic acid, crystalline Lucerastat: Fumaric acid, crystalline Lucerastat: Benzoic acid and crystalline Lucerastat: o-Acetylsalicylic acid, may be formulated for administration to a mammal, in embodiments to a human, by injection. Crystalline Lucerastat: L-pyroglutamic acid, crystalline Lucerastat: Salicylic acid, crystalline Lucerastat: Fumaric acid, crystalline Lucerastat: Benzoic acid and crystalline Lucerastat: o-Acetylsalicylic acid can be formulated, for example, as a viscous liquid solution or suspension, such as a clear solution, for injection. The formulation can contain one or more solvents. A suitable solvent can be selected by considering the solvent's physical and chemical stability at various pH levels, viscosity (which would allow for syringeability), fluidity, boiling point, miscibility, and purity. Suitable solvents include alcohol USP, benzyl alcohol NF, benzyl benzoate USP, and Castor oil USP. Additional substances can be added to the formulation such as buffers, solubilizers, and antioxidants, among others. Ansel et al., Pharmaceutical Dosage Forms and Drug Delivery Systems, 7th ed.

The crystalline polymorphs of Lucerastat: L-pyroglutamic acid, Lucerastat: Salicylic acid, Lucerastat: Fumaric acid, Lucerastat: Benzoic acid and Lucerastat: o-Acetylsalicylic acid, and the pharmaceutical compositions and/or formulations of crystalline Lucerastat: L-pyroglutamic acid, crystalline Lucerastat: Salicylic acid, crystalline Lucerastat: Fumaric acid, crystalline Lucerastat: Benzoic acid and crystalline Lucerastat: o-Acetylsalicylic acid, of the present disclosure can be used as medicaments, in embodiments in the treatment of Fabry disease.

The present disclosure also provides methods of treating Fabry disease by administering a therapeutically effective amount of any one or a combination of the crystalline polymorph Lucerastat: L-pyroglutamic acid, Lucerastat: Salicylic acid, Lucerastat: Fumaric acid, Lucerastat: Benzoic acid and Lucerastat: o-Acetylsalicylic acid, of the present disclosure, or at least one of the above pharmaceutical compositions and/or formulations, to a subject in need of the treatment.

Having thus described the disclosure with reference to particular preferred embodiments and illustrative examples, those in the art can appreciate modifications to the disclosure as described and illustrated that do not depart from the spirit and scope of the disclosure as disclosed in the specification. The Examples are set forth to aid in understanding the disclosure but are not intended to, and should not be construed to limit its scope in any way.

Powder X-Ray Diffraction ("XRPD") Method

X-ray diffraction was performed on X-Ray powder diffractometer: Bruker D8 Advance; CuKα radiation (λ=1.54187 Å); Lynx eye detector; laboratory temperature 22-25° C.; PMMA specimen holder ring. Prior to analysis, the samples were gently ground by means of mortar and pestle in order to obtain a fine powder. The ground sample was adjusted into a cavity of the sample holder and the surface of the sample was smoothed by means of a cover glass.

Measurement Parameters:

Scan range: 2-40 degrees 2-theta;

Scan mode: continuous;

Step size: 0.05 degrees;

Time per step: 0.5 s;

Sample spin: 30 rpm;

Sample holder: PMMA specimen holder ring.

All X-Ray Powder Diffraction peak values are calibrated with regard to standard silicon spiking in the sample.

Dynamic Vapour Sorption ("DVS") Method 10-50 mg of Sample was added to quartz sample pan. The two RH cycles (Sorption and Desorption) were performed at 25° C. In each cycle, RH was raised in 10 steps, from 0% to 95% (0, 10, 20, 30, 40, 50, 60, 70, 80 and 95%) and then back to 0% (95, 80, 70, 60, 50, 40, 30, 20, 10 and 0%). A rate of change in mass per time unit (dm/dt) of 0.002%/min was set as the equilibration parameter. At each stage, the set parameters were held until the mass change reaches to 0.002%/min (i.e. equilibrium conditions). Measurements were carried out at room temperature.

EXAMPLES

Preparation of Starting Materials

Lucerastat can be prepared according to methods known from the literature, for example Lucerastat Form 1 can be prepared according to U.S. Pat. No. 6,291,657 and International Publication No. WO 2018/220131.

Example 1: Preparation of Crystalline Lucerastat: L-Pyroglutamic Acid Form LC-1

Lucerastat (Form 1, 100 mg) and L-pyroglutamic acid (56.88 mg) in 1:1 molar ratio was taken into 5 mL test tube, added 2 mL of Dichloromethane and the slurry was stirred at 400 rpm at 25-30° C. for 2 hours. The obtained solid was filtered under vacuum at 25-30° C. and kept for suction for 5 to 10 minutes at same temperature. The obtained material, crystalline Lucerastat: L-pyroglutamic acid Form LC-1 was confirmed by XRPD.

Example 2: Preparation of Crystalline Lucerastat: L-Pyroglutamic Acid Form LC-1

Lucerastat (Form 1, 100 mg) and L-pyroglutamic acid (56.88 mg) in 1:1 molar ratio was taken into 5 mL test tube, added 2 mL of Acetonitrile and the slurry was stirred 400 rpm at 60° C. for 30 minutes and then at 25-30° C. for 1 hour. The obtained solid was filtered under vacuum at 25-30° C. and kept for suction for 5 to 10 minutes at same temperature. The obtained material, crystalline Lucerastat-L-pyroglutamic acid Form LC-1 was confirmed by XRPD.

Example 3: Preparation of Crystalline Lucerastat: Salicylic Acid Form LC-2

Lucerastat (Form 1, 1000 mg) and Salicylic acid (630 mg) in 1:1 molar ratio were taken into 20 mL test tube, added 10 mL of Acetonitrile and heated to 60° C. under stirring at 800 rpm for 30 minutes to dissolve. The obtained clear solution was filtered through 0.45 μ syringe filter and cooled to 25° C. in 15 minutes. The clear solution was stirred at 25° C. (at 400 rpm) for 3 hours. The obtained solid was filtered under vacuum at 25-30° C. in presence of nitrogen atmosphere and kept for drying using suction for about 10 to 15 minutes at same temperature. Crystalline Lucerastat: Salicylic acid Form LC-2 content was confirmed by XRPD (FIG. 2).

Example 4: Preparation of Crystalline Lucerastat: Salicylic Acid Form LC-2

Lucerastat (Form 1, 50 mg) and Salicylic acid (31.5 mg) in 1:1 molar ratio were taken into 2 mL test tube, added 0.5 mL of Acetone and heated to 50° C. under stirring at 800 rpm for 30 minutes to dissolve. The obtained clear solution was cooled to 25° C. in 15 minutes and stirred at 25° C. at 800 rpm for 1 hour and then further cooled to 0-5° C. and kept with stirring for 66 hours. The obtained solid was filtered under vacuum at 0-5° C. in presence of nitrogen atmosphere and kept for drying using suction for about 5 to 10 minutes at 25-30° C. Crystalline Lucerastat: Salicylic acid Form LC-2 content was confirmed by XRPD.

Example 5. Preparation of Crystalline Lucerastat: Salicylic Acid Form-LC-2

Lucerastat (Form 1, 50 mg) and Salicylic acid (31.5 mg) in 1:1 molar ratio were taken into 2 mL test tube, added 0.5 mL of Methyl Ethyl Ketone and heated to 60° C. under stirring at 800 rpm for 30 minutes to dissolve. The obtained clear solution was cooled to 25° C. in 15 minutes and stirred at 25° C. at 800 rpm for 1 hour and then further cooled to 0-5° C. and kept for stirring at this temperature for additional 66 hours. The obtained solid was filtered under vacuum at 0-5° C. in presence of nitrogen atmosphere and kept for drying by using suction for about 5 to 10 minutes at 25-30° C. Crystalline Lucerastat: Salicylic acid Form LC-2 content was confirmed by XRPD.

Example 6. Preparation of Crystalline Lucerastat: Salicylic Acid Form LC-2

Lucerastat (Form 1, 50 mg) and Salicylic acid (31.5 mg) in 1:1 molar ratio were taken into 10 mL test tube, added 1 mL of Acetonitrile and heated to 60° C. under stirring at 800 rpm for 30 minutes to dissolve. The obtained clear solution was cooled to 25° C. in 15 minutes and stirred at 25° C. at 400 rpm for 16 hours. The obtained solid was filtered under vacuum at 25-30° C. in presence of nitrogen atmosphere and kept for drying using suction for about 5 to 10 minutes at same temperature. Crystalline Lucerastat: Salicylic acid Form LC-2 content was confirmed by XRPD.

Example 7. Preparation of Crystalline Lucerastat: Fumaric Acid Form LC-3

Lucerastat (Form 1, 50 mg) and Fumaric acid (26.5 mg) in 1:1 molar ratio was taken into 10 mL test tube, added 2 mL of Acetonitrile and heated to 60° C. under stirring at 800 rpm for 30 minutes. The obtained slurry (looks like gummy mass) was cooled to 25° C. in 15 minutes and stirred at 25° C. at 800 rpm for 21 hours. The obtained solid was filtered under vacuum at 25-30° C. in presence of nitrogen atmosphere and kept for drying using suction for about 5 to 10 minutes at same temperature. Crystalline Lucerastat: Fumaric acid Form LC-3 content was confirmed by XRPD (FIG. 3).

Example 8. Preparation of Crystalline Lucerastat: Fumaric Acid Form LC-3

Lucerastat (Form 1, 500 mg) and Fumaric acid (265 mg) in 1:1 molar ratio was taken into 20 mL test tube, added 10 mL of Acetonitrile and stirred the slurry 25° C. at 400 rpm for 3 hours. The obtained solid was filtered under vacuum at 25-30° C. in presence of nitrogen atmosphere and kept for drying using suction for about 10 to 15 minutes at same temperature. Crystalline Lucerastat: Fumaric acid Form LC-3 content was confirmed by XRPD.

Example 9. Preparation of Crystalline Lucerastat: Benzoic Acid Form LC-4

Lucerastat (Form 1, 50 mg) and Benzoic acid 27.8 mg in 1:1 molar ratio was taken into 2 mL vial, added 0.5 mL of Acetonitrile and the slurry was stirred at 800 rpm at 25-30° C. for 1.5 Hrs. The obtained solid was filtered under vacuum at 25-30° C. in presence of nitrogen atmosphere and kept for suction for about 5 to 10 minutes at same temperature. Crystalline Lucerastat: Benzoic Form LC-4 content was confirmed by XRPD (FIG. 4).

Example 10. Preparation of Crystalline Lucerastat: o-Acetylsalicylic Acid Form LC-5

Lucerastat (Form 1, 50 mg) and o-Acetylsalicylic acid 41.1 mg in 1:1 molar ratio was taken into 2 mL vial, added 0.5 mL of Acetonitrile and heated to 60° C. and maintained at 60° C. for 30 minutes. Clear solution was further cooled to 25-30° C. and stirred at same temperature for hour and 0-5° C. for 66 hours. Finally clear solution kept at 25-30° C. for slow solvent evaporation for 7 days. Crystalline Lucerastat: 0-Acetylsalicylic acid Form LC-5 was analyzed by XRPD (FIG. 5).

The invention claimed is:

1. A crystalline Form LC-1 of L-pyroglutamic acid salt of Lucerastat, which is characterized by data selected from one or more of the following:

a) an XRPD pattern having peaks at 10.1, 13.3, 16.3, 20.3 and 30.7 degrees 2-theta ±0.2 degrees 2-theta; and/or b) an XRPD pattern as depicted in FIG. 1.

2. The crystalline Form LC-1 of L-pyroglutamic acid salt of Lucerastat according to claim 1, characterized by an XRPD pattern having peaks at 10.1, 13.3, 16.3, 20.3 and 30.7 degrees 2-theta ±0.2 degrees 2-theta, and also having one, two, three, four or five additional peaks selected from 8.3, 14.5, 18.4, 21.8 and 22.9 degrees two theta ±0.2 degrees two theta.

3. The crystalline Form LC-1 of L-pyroglutamic acid salt of Lucerastat according to claim 1, characterized by an XRPD pattern having peaks at 8.3, 10.1, 13.3, 14.5, 16.3, 18.4, 20.3, 21.8, 22.9 and 30.7 degrees 2-theta ±0.2 degrees 2-theta.

4. A crystalline Form LC-2 of Salicylic acid salt of Lucerastat, which is characterized by data selected from one or more of the following:

a) an XRPD pattern having peaks at 5.2, 16.6, 18.2, 22.3 and 23.7 degrees 2-theta ±0.2 degrees 2-theta; and/or b) an XRPD pattern as depicted in FIG. 2.

5. The crystalline Form LC-2 of Crystalline Salicylic acid salt of Lucerastat according to claim 4, characterized by an XRPD pattern having peaks at 5.2, 16.6, 18.2, 22.3 and 23.7 degrees 2-theta ±0.2 degrees 2-theta, and also having one, two, three, four or five additional peaks selected from 17.3, 19.5, 25.5, 22.9 and 34.2 degrees two theta ±0.2 degrees two theta.

6. The crystalline Form LC-2 of Salicylic acid salt of Lucerastat according to claim 4, characterized by an XRPD pattern having peaks at 5.2, 16.6, 17.3, 18.2, 19.5, 22.3, 22.9, 23.7, 25.5 and 34.2 degrees 2-theta ±0.2 degrees 2-theta.

7. The crystalline Form LC-2 of Salicylic acid salt of Lucerastat according to claim 4 containing less than 10 wt % water.

8. The crystalline Form LC-2 of Salicylic acid salt of Lucerastat according to claim 4, which is non-deliquescent.

9. A pharmaceutical formulation comprising the crystalline Form LC-2 of Salicylic acid salt of Lucerastat according to claim 4 in the form of a tablet, capsule, or solution for injection.

10. A medicament comprising the crystalline Form LC-2 of Salicylic acid salt of Lucerastat according to claim 4.

11. A method of treating Fabry disease, comprising administering a therapeutically effective amount of the crystalline Form LC-2 of Salicylic acid salt of Lucerastat according to claim 4 to a subject in need of treatment.

* * * * *